US007220381B2

(12) United States Patent
Ting et al.

(10) Patent No.: US 7,220,381 B2
(45) Date of Patent: May 22, 2007

(54) METHOD FOR HIGH PRESSURE TREATMENT OF SUBSTANCES UNDER CONTROLLED TEMPERATURE CONDITIONS

(75) Inventors: Edmund Y. Ting, Kent, WA (US); Nils-Gunnar Lönneborg, Västerås (SE); Anders Träff, Västerås (SE)

(73) Assignee: Avure Technologies Incorporated, Kent, WA (US)

( * ) Notice: Subject to any disclaimer, the term of this patent is extended or adjusted under 35 U.S.C. 154(b) by 917 days.

(21) Appl. No.: 09/883,091

(22) Filed: Jun. 15, 2001

(65) Prior Publication Data

US 2002/0192109 A1    Dec. 19, 2002

(51) Int. Cl.
*A61L 2/02*    (2006.01)

(52) U.S. Cl. .............................. 422/1; 422/38; 426/521

(58) Field of Classification Search .................... 422/1, 422/38, 39, 242, 307; 426/521, 665
See application file for complete search history.

(56) References Cited

U.S. PATENT DOCUMENTS

| 2,611,585 | A | 9/1952 | Boling ........................ 257/241 |
| 2,680,802 | A | 6/1954 | Bremer et al. ................. 219/40 |
| 2,687,626 | A | 8/1954 | Bartlowe ..................... 62/126 |
| 4,160,408 | A | 7/1979 | Ulvestad ..................... 99/348 |
| 4,313,370 | A | 2/1982 | Skoli et al. ................. 99/323.1 |
| 4,334,141 | A | 6/1982 | Roller et al. ................. 219/283 |
| 4,439,112 | A | 3/1984 | Kitsnik ....................... 417/383 |
| 4,625,789 | A | 12/1986 | Chaix et al. ............... 165/11.1 |
| 4,659,472 | A | 4/1987 | Nordlund et al. ........... 210/609 |
| 4,695,472 | A | 9/1987 | Dunn et al. .................. 426/237 |
| 4,789,313 | A | 12/1988 | Tower et al. ................ 417/388 |
| 5,048,404 | A | 9/1991 | Bushnell et al. .............. 99/451 |
| 5,075,124 | A | 12/1991 | Horie et al. ................. 426/577 |
| 5,213,029 | A | 5/1993 | Yutaka ......................... 99/474 |
| 5,229,150 | A | 7/1993 | Ahnell et al. ............... 426/231 |
| 5,232,726 | A | 8/1993 | Clark et al. ................. 426/519 |
| 5,235,905 | A | 8/1993 | Bushnell et al. .............. 99/451 |
| 5,257,341 | A | 10/1993 | Austin, Jr. et al. .......... 392/487 |
| 5,265,318 | A | 11/1993 | Shero .......................... 29/447 |

(Continued)

FOREIGN PATENT DOCUMENTS

DE    42 26 767 C1    9/1993

(Continued)

OTHER PUBLICATIONS

Hayakawa et al., "Application of High Pressure for Spore Inactivation and Protein Denaturation," *J. of Food Science* 59(1):159-163, 1994.

(Continued)

*Primary Examiner*—E. Leigh McKane
(74) *Attorney, Agent, or Firm*—Harness, Dickey & Pierce, P.L.C.

(57) ABSTRACT

A product carrier for use in pressure processing substances is substantially fluidically closed, and is insulated, to prevent heat transfer from the product being treated to the cooler wall of the pressure vessel. The insulating material has compression heating properties, such that as the product is pressurized, the temperature of the insulation increases as does the temperature of the product and pressure media, thereby helping to prevent heat transfer from the product to the surrounding media and pressure vessel wall.

15 Claims, 2 Drawing Sheets

U.S. PATENT DOCUMENTS

| | | | |
|---|---|---|---|
| 5,393,547 A | 2/1995 | Balaban et al. | 426/330 |
| 5,394,505 A | 2/1995 | Bidare | 392/379 |
| 5,439,703 A | 8/1995 | Kanda et al. | 426/665 |
| 5,458,901 A | 10/1995 | Engler et al. | 426/521 |
| 5,475,983 A | 12/1995 | Yamamoto et al. | 62/62 |
| 5,571,476 A | 11/1996 | Newman | 422/26 |
| 5,579,682 A | 12/1996 | Bergman et al. | 99/473 |
| 5,658,610 A | 8/1997 | Bergman et al. | 426/665 |
| 5,724,478 A | 3/1998 | Thweatt | 392/484 |
| 6,017,572 A | 1/2000 | Meyer | 426/521 |
| 6,086,936 A | 7/2000 | Wilson et al. | 426/521 |
| 6,177,115 B1 * | 1/2001 | Meyer | 426/521 |
| 6,217,435 B1 | 4/2001 | Voisin | 452/12 |
| 6,283,832 B1 | 9/2001 | Shepherd | 451/40 |
| 6,330,395 B1 | 12/2001 | Wu | 392/494 |
| 6,393,977 B1 | 5/2002 | Voisin | 99/467 |
| 6,426,103 B2 | 7/2002 | Voisin | 426/113 |
| 6,442,341 B1 | 8/2002 | Wu | 392/479 |
| 6,537,601 B1 | 3/2003 | Voisin | 426/113 |
| 6,632,941 B2 | 10/2003 | Wooten et al. | 536/127 |
| 2001/0041206 A1 | 11/2001 | Raghavan et al. | 426/523 |
| 2002/0006465 A1 | 1/2002 | Voisin | 426/643 |
| 2003/0161917 A1 | 8/2003 | Voisin | 426/410 |

FOREIGN PATENT DOCUMENTS

| | | |
|---|---|---|
| DE | 44 06 028 A1 | 8/1995 |
| GB | 338740 | 11/1930 |
| GB | 395709 | 7/1933 |
| JP | 62-66862 | 3/1987 |
| JP | 62-122546 | 6/1987 |
| JP | 1-110362 | 4/1989 |
| JP | 1-196251 | 8/1989 |
| JP | 2-89598 | 3/1990 |
| JP | 2-182157 | 7/1990 |
| JP | 2-245146 | 9/1990 |
| JP | 3-147772 | 6/1991 |
| JP | 3-292863 | 12/1991 |
| JP | 4-63569 | 2/1992 |
| JP | 4-299967 | 10/1992 |
| JP | 4-356156 | 12/1992 |
| JP | 5-161483 | 6/1993 |
| JP | 6-7135 | 1/1994 |
| WO | WO 92/22748 | 12/1992 |
| WO | WO 94/21145 | 9/1994 |
| WO | WO 96/11588 | 4/1996 |
| WO | WO 97/21361 | 6/1997 |
| WO | WO 99/29187 | 6/1999 |
| WO | WO 99/38394 | 8/1999 |
| WO | WO 00/64493 | 11/2000 |
| WO | WO 01/10773 A1 | 2/2001 |
| WO | WO 02/45528 A1 | 6/2002 |
| WO | WO2004/082405 A1 * | 9/2004 |

OTHER PUBLICATIONS

Hayakawa et al., "Oscillatory Compared with Continuous High Pressure Sterilization on Bacillus stearothermophilus Spores," *J. of Food Science* 59(1):164-167, 1994.

Heremans (ed), *High Pressure Research in the Biosciences and Biotechnology*, Leuven University Press, Leuven, Belgium, 1997, "Microbiological stabilisation of low acid food using a combined high pressure-temperature process," pp. 277-280.

Maggi et al., "Effects of Combined High Pressure-Temperature Treatments on Clostridium Sporogenes Spores in Liquid Media," *Ind. Conserve* 71:8-14, 1996.

Meyer et al., "High-Pressure Sterilization of Foods," *Food Technology* 54(11):67-72, 2000.

Rovere et al., "High-Pressure Heat Treatments: Evaluation of the Sterilizing Effect and of Thermal Damage," *Ind. Conserve* 71:473-483, 1996.

P. Rovere, "The Third Dimension of Food Technology, Next to time and temperature, a new and revolutionary operative parameter: high pressure," *Technologie Alimentari, Sistemi per Produrre*, No. 4, 1995.

* cited by examiner

METHOD FOR HIGH PRESSURE TREATMENT OF SUBSTANCES UNDER CONTROLLED TEMPERATURE CONDITIONS

TECHNICAL FIELD

This invention relates to the high pressure treatment of substances, for example, food products, and more particularly, to the high pressure treatment of substances under controlled temperature conditions.

BACKGROUND OF THE INVENTION

It is well known that pathogens and microorganisms in substances, for example, food, may be inactivated by exposing the substances to high pressure. It is also well understood that for some applications, for example, for microorganisms that are difficult to inactivate, the effectiveness of the pressure processing can be enhanced by the use of elevated temperatures.

Using currently available systems and methods, a substance to be treated is placed in a container, typically a perforated basket made from stainless steel or plastic. The perforated basket and its contents are placed into a pressure vessel and exposed to a pressure media, typically high pressure water, for a selected period of time. The pressure vessel is then depressurized, and the pressure treated substance is removed from the pressure vessel. Because the basket is perforated, the pressure media flows through the side walls of the basket and surrounds the substance to be treated.

While current methods provide acceptable results in many situations, it is believed that improved results can be achieved, particularly for difficult microorganisms, such as bacteria spores. Thus, the present invention is directed to improving the efficacy of current systems in destroying undesirable pathogens and microorganisms in a substance.

SUMMARY OF THE INVENTION

Briefly, the present invention improves the efficacy of the pressure processing of substances by providing an insulated carrier into which is placed the substance to be treated. Applicants believe that the ability of current methods to inactivate targeted microorganisms, especially difficult ones like bacteria spores, is reduced by the loss of heat from the product to the vessel. More particularly, during the pressurization cycle, the product and pressure media get hotter due to compression or adiabatic heating. Because the walls of the pressure vessel do not experience a similar increase in temperature, there is a temperature difference between the vessel wall and the product under treatment. As a result, heat flows from the product, reducing the ability of the pressure process to inactivate microorganisms.

Therefore, the present invention improves the efficacy of a pressure treatment process by providing an insulated enclosure into which is placed a substance or product to be treated. The enclosure has solid side walls, a top closure, and a floor that define an outer surface of the enclosure that is substantially fluidically closed. Pressure media entry ports are provided in the enclosure, and in a preferred embodiment, valves are positioned in the ports to selectively allow pressure media to enter the enclosure.

The enclosure is insulated by providing a quantity of insulating material around an inner region of the enclosure. Any low conductivity material may be used for insulation, for example, polyethylene, polypropylene, polyvinylchloride, or rubber. In a preferred embodiment, the insulating material has substantially high adiabatic heating properties, such that the temperature of the insulation increases during the pressurization cycle. For example, ultrahigh molecular weight polyethylene (UHMWPE), at 25° C. exhibits a compression temperature change of 5° C. per 100 MPa pressure change. Low density polyethylene at 25° C. exhibits an adiabatic compression temperature change of 7° C. per 100 MPa pressure change, and natural rubber at 25° C. exhibits a compression temperature change of 8° C. per 100 MPa pressure change. By insulating the product carrier, heat loss from the product chamber to the metal pressure vessel is substantially minimized during the pressure cycle. Using an insulating material with high adiabatic heating properties generates a temperature barrier to further prevent heat transfer from the product chamber to the vessel wall. Also, by using a carrier that is substantially fluidically closed, as compared to conventional perforated baskets, the circulation of pressure media from the product to the vessel wall is substantially prevented.

The insulated product carrier may be used in various methods designed to improve the effectiveness of the pressure process. For example, in one preferred embodiment, the substance to be treated is preheated prior to being placed in the pressure vessel. Although this may be accomplished in a variety of ways, in one embodiment, the carrier loaded with product is placed into a warm circulating fluid bath until the product reaches a desired temperature. By way of a second example, rapid heating methods may be used, such as microwave heating. The pressure vessel is also preheated, for example, through the use of heating elements coupled to the vessel or by a heating jacket provided around the vessel, or by the circulation of hot water in the pressure vessel. If desired, the pressure media, for example, ultrahigh-pressure water, may also be preheated to the selected temperature. After preheating the product, vessel and media, the product carrier is transferred to the pressure vessel where it is subjected to the heated pressure media. After being pressurized for a selected period of time, the product carrier and its contents are removed from the pressure vessel and, if desired, the contents placed in a cooling apparatus, for example, a cool water bath or a refrigerated space.

In another preferred embodiment, the pressure vessel is preheated to a temperature that is higher than the starting temperature of the product prior to pressurization. Assuming certain pressure characteristics of the substance being treated, the vessel is preheated to a temperature the product is expected to reach upon being pressurized. A high vessel wall temperature will prevent heat loss from the product. The presence of the insulating carrier will reduce the amount of heat transferred to the product prior to the start of pressurization.

DETAILED DESCRIPTION OF THE INVENTION

Many objectives may be achieved by exposing a substance to ultrahigh-pressure. Such pressure processing may be used, for example, to pasteurize or sterilize a substance, such as a medical or food product. Although the selected pressure will vary depending on the application, pressures in the range of 40,000-130,000 psi are often used and thought of when referring to ultrahigh-pressure processing. It will be understood that other variables in the process are also selected according to the application, as determined by one of ordinary skill in the art. These other variables include such things as the temperature at which the substance is processed and the amount of time the substance is held under pressure, commonly referred to as the dwell time.

Current pressure processing of a substance, for example, to destroy microorganisms, can be done in a continuous flow process or in batches. In conventional batch processing, the product or substance to be pressure treated is placed into a perforated basket that is in turn placed into a pressure vessel filled with pressure media, for example, water. The pressure vessel is closed and pressurized to a selected pressure, which pressure is held for a selected period of time. The pressure vessel is then depressurized and the treated product is removed from the pressure vessel. The product carrier, being perforated, is substantially fluidically open, allowing the pressure media to flow through the carrier and around the product. The free flow of fluid through the product carrier facilitates the transfer of heat from the product and pressure media to the vessel wall.

Figure 1:
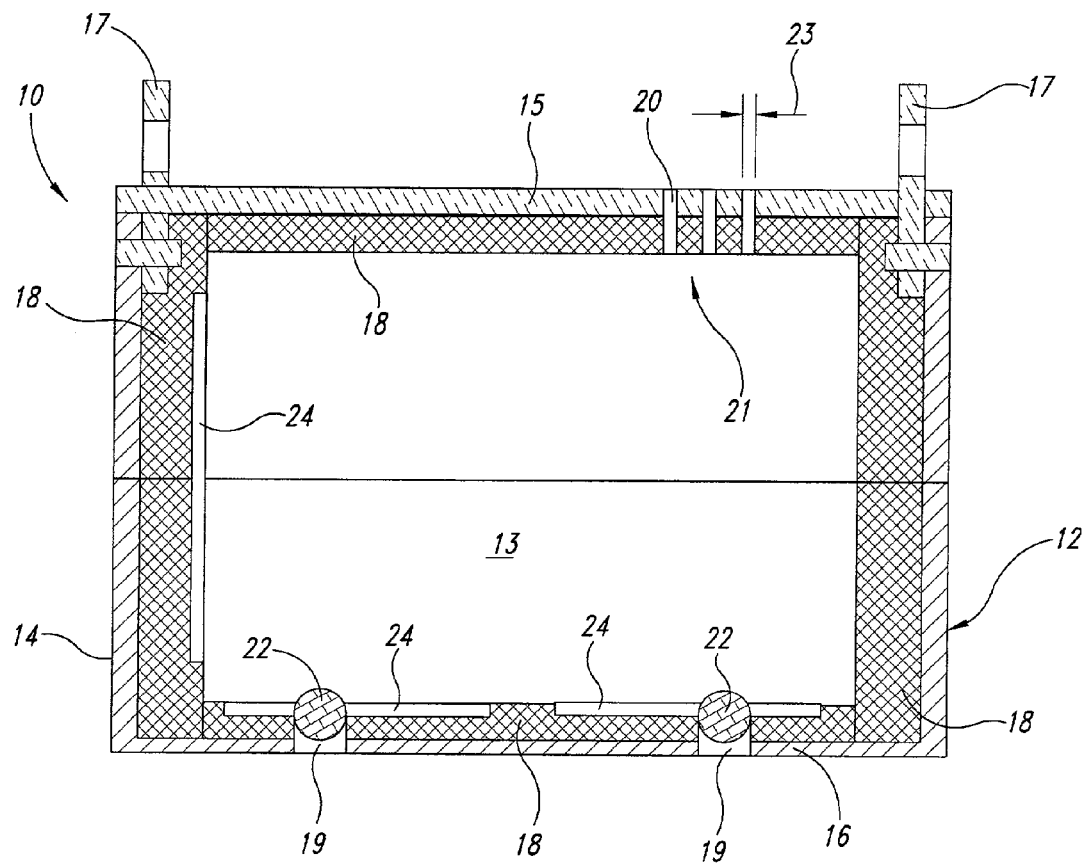
FIG. 1 is a cross-sectional elevational view of an insulated carrier provided in accordance with the present invention.

As discussed previously, applicants believe that the rise in temperature in the product and pressure media during compression, creating a temperature gradient between the product and the metal vessel wall, results in a loss of heat from the product. This loss of heat in the product reduces the effectiveness of the process to kill microorganisms. Therefore, in a preferred embodiment of the present invention, as illustrated in FIG. 1, a carrier 10 has outer side walls 14, a top closure 15, and a floor 16 defining an enclosure 12 that is substantially fluidically closed. An inner region of the carrier 10 is open to form chamber 13, into which is placed the substance or product 11 to be treated. Brackets 17 coupled to the carrier 10 enable the carrier to be transported between various stations in the pressure processing cycle, as will be discussed in greater detail below.

In accordance with a preferred embodiment of the present invention, a quantity of insulating material 18 is provided around an inner region of the enclosure 12. In a preferred embodiment the insulating material has relatively high adiabatic heating properties, namely, at 25° C., it exhibits a compression temperature change of 3-10° C. per 100 MPa pressure change. Examples of appropriate insulating materials include polyethylene, polypropylene, polyvinylchloride, and rubber.

As further seen in FIG. 1, the carrier 10 is provided with a plurality of pressure media entry ports 19. In a preferred embodiment, as shown in FIG. 1, the pressure media entry ports 19 are provided in the floor 16 of the enclosure to be proximal the inlet port through which temperature controlled water is pumped into the vessel for pressurization. Proximity of the point-of-entry of media into the vessel and the point-of-entry of media into the carrier allows water to enter into the carrier almost immediately after entering the pressure vessel, to minimize the temperature change of the media. However, it will be understood that the pressure media entry ports 19 may be provided in other locations, such as the side walls 14 or top closure 15. In a preferred embodiment, a check valve 22 is positioned in each pressure media entry port 19 to further control the flow of fluid into and out of the product carrier 10. To further assist the distribution of pressure media, a plurality of grooves 24 are provided in the insulating material 18.

A plurality of air vents 20 are provided in an upper region 21 of the enclosure. A dimension of the air vents, for example, diameter 23, is sufficiently small relative to the size of the chamber 13 to reduce convection currents between the inside of the carrier and the chamber 13. The diameter of the vent should be typically less than 0.25". Alternatively, a check valve may be positioned in the top of the carrier, that allows fluid to flow only out of the carrier. Such a check valve should be of sufficient size to allow depressurization of the carrier during depressurization of the pressure chamber, without undue overpressure of the carrier.

By providing a carrier 10 that is substantially fluidically closed and that is insulated, the amount of heat loss from the product to the metal vessel is reduced. By using an insulating material which increases in temperature during compression similar to the temperature rise in the product and pressure media, a temperature barrier is generated to further prevent heat transfer from the product chamber 13 to the wall of pressure vessel 26. By maintaining the temperature of the product at a desired level, the ability of the process to inactivate microorganisms is improved.

Adiabatic compression of water-like substances at 25° C. will generate a temperature increase of approximately 3° C. per 100 MPa of compression. Many products, particularly food products, have compression heating characteristics similar to that of water, and it is therefore appropriate and cost effective to use water as the pressure media. However, if the product to be treated has compression heating characteristics greater than that of water, namely, they experience a greater temperature change than water for a given pressure increase, the pressure media can be selected to match the compression heating properties of the product. By matching the compression heating properties of the product and the pressure media, heat transfer from the product to the pressure media is substantially prevented. For example, a product having a high fat content may be pressurized using a pressure media of a water/alcohol or glycol/water solution to achieve comparable compression heating.

In a preferred embodiment, the outer walls 14 are made of a rigid material to provide structural strength to the product carrier 10. Although a variety of materials may be used, in a preferred embodiment, walls 14 are made from stainless steel or PVC. By having a strong external structure, the product carrier may be lifted and moved while fully loaded, without deforming. It will, of course, be understood that it may be possible to combine the insulating function and the need for structural strength depending on the size and weight of the carrier in a particular application. For example, it may be possible to use a stiff plastic, such as PVC, to provide the insulating feature and provide the necessary structural strength to allow the loaded carrier to be moved between stations in the process without deforming.

Figure 2:
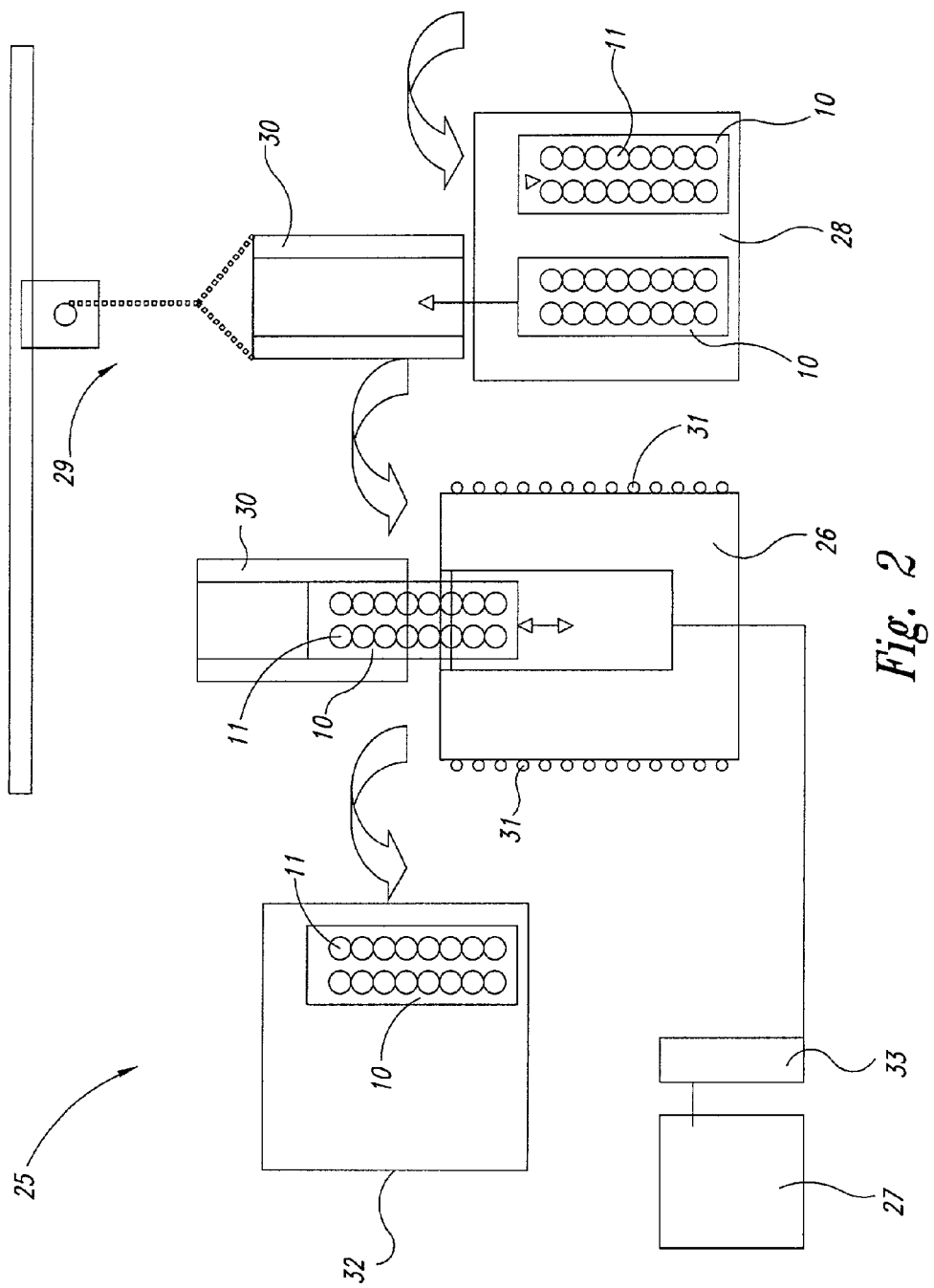
FIG. 2 is a schematic elevational view of an assembly provided in accordance with the present invention.

In operation, as shown in FIG. 2, the product 11 is loaded into a product carrier 10, shown schematically in FIG. 2 for simplicity. It will be understood that devices may be used within the carrier as desired to align products depending on the physical shape and size of the product. Once loaded, the product carrier 10 is inserted into the pressure vessel 26 where it is exposed to a volume of ultrahigh-pressure fluid from a source of ultrahigh-pressure fluid 27, for example an ultrahigh-pressure pump, such as those manufactured by Flow International Corporation. The product carrier and its contents are held within the pressure vessel 26 at the elevated pressure for a selected period of time, after which the pressure is released, and the product carrier 10 is removed from the pressure vessel.

In a preferred embodiment, the pressure-processing assembly 25 includes a preheating apparatus 28. The product 11 is preheated by placing the carrier 10 in the preheating apparatus 28, for example, a hot water bath, for a period of time necessary for the product to reach a desired temperature. In a preferred embodiment, the pressure media entry port 19 is designed to mate with the preheating device so as to direct preheated water into the carrier to preheat the product within the carrier.

Simultaneous with preheating the product 11, the pressure vessel 26 is preheated to the desire temperature through the use of heating elements 31 coupled to the vessel 26. To further improve the efficiency of the system, the ultrahigh-pressure fluid 27 is preheated to the selected temperature through a heating device 33. In a preferred embodiment, device 33 includes a plurality of heat-exchanger blocks through which ultrahigh-pressure tubing passes, the pressure media flowing from an ultrahigh-pressure pump to the pressure vessel through the ultrahigh-pressure tubing. Such a heating system is more fully described and claimed in co-pending U.S. patent application Ser. No. 09/883,090, entitled "Method and Apparatus for Changing the Temperature of a Pressurized Fluid," now issued as U.S. Pat. No. 6,804,459, and assigned to Flow International Corporation, which patent is incorporated by reference into the present application.

By preheating the pressure media, the pressure vessel 26, and the product 11 to the same temperature, the product is in a steady state with no heat transfer, prior to pressurization. However, as described above, during the pressurization and pressure hold period, the temperature of the pressure media and product will increase to a temperature greater than that of the vessel wall. By using an insulated carrier 10, as described above, temperature loss from the product is substantially prevented.

If desired, the product carrier 10 and or product 11 contained therein may be placed in a cooling apparatus 32 after it is removed from the pressure vessel 26. The product carrier 10 is moved between the various stations, for example, from the preheating apparatus 28 to the pressure vessel 26 and cooling apparatus 32, via a transport mechanism 29. If desired, the transport mechanism 29 may include an insulated holder 30 that insulates the product carrier 10 to further prevent heat loss as the product carrier 10 is transferred from the preheating apparatus 28 to the pressure vessel 26. Because the insulated holder 30 is not subjected to pressure, it may be constructed with conventional insulating materials, for example, with expanded foam, fiberglass, or other air-trapping insulation materials. The insulating material is preferably hermetically sealed, to prevent moisture from the product carrier 10 from penetrating the insulation of the holder 30.

Alternatively, it may be desirable to preheat the pressure vessel 26 to a temperature that is higher than the starting temperature of the product prior to pressurization. In a preferred embodiment, the temperature of the vessel 26 is set to the temperature the product 11 is expected to reach upon pressurization. For example, if the product to be treated has water-like compression heating characteristics, it may be assumed that at 25° C., the product will experience a 3° C. temperature increase for every 100 MPa of compression. If it is determined that the pressurization will be carried out at 600 MPa, the final temperature will be 18° C. higher than the starting temperature. This approach may be well suited for applications in which there is a long hold time, to ensure that no heat transfer from the product to the vessel takes place. However, when using this method, it is desirable to place the product carrier 10 into the vessel 26 and simultaneously fill the vessel 26 with pressure media so that the pressure vessel 26 can be closed and pressurized quickly so as to prevent significant heat transfer from the vessel to the colder pressure media and product 11 prior to pressurization. The insulated carrier will prevent heat transfer from the hotter vessel wall to the cooler product during the period prior to pressurization.

To further aid the speed with which the pressurization process may take place, in a preferred embodiment, a quantity of pressure media 27 is placed into the product carrier 10 with the product, prior to inserting the product carrier 10 into the pressure vessel 26. It will be understood, however, that if pressure media is transferred from the preheating apparatus to the pressure vessel in the carrier 10, it is necessary to provide fluid isolation valves in the pressure media entry ports 19, for example, check valves 22.

The importance of temperature stability is greater at higher operating temperatures than at lower operating temperatures. Therefore, while not limiting the invention in any way, the embodiments described herein may be particularly well suited to applications where the starting temperature of the substance to be treated, prior to pressurization, is substantially 60-100° C.

To further control the temperature of the pressure media, it may be desirable to evacuate the pressure vessel 26 between batches. For example, after a pressure cycle occurs and the product carrier 10 is removed from the pressure vessel, the water or other pressure media is removed and collected in a reservoir 27, where it is again heated to a selected temperature. Once the desired temperature is reached, the water is returned to the pressure vessel 26 prior to or simultaneous with the product carrier 10 loaded with a new batch of product being placed into the pressure vessel. Alternatively, it may be desirable to discharge the pressure media from the reservoir to the vessel 26 after the carrier 10 is loaded into the vessel to prevent loss of heat in the pressure media.

Also, in a preferred embodiment, a plurality of thermocouples are mounted to the carrier to monitor the internal temperature of the carrier. The thermocouples may be coupled to a feedback control loop, as is known in the art, to monitor and adjust the temperature of the process as may be desired. Although any number of thermocouples and method of coupling may be used, in a preferred embodiment, four thermocouples coupled to the carrier are aligned with thermocouple connectors coupled to an upper closure of the pressure vessel, such that the thermocouples are automatically engaged upon closure of the vessel.

In an alternative embodiment, an insulated carrier is applied to low temperature processing. Applicants believe there may be some situations in which low temperature processing will achieve desired results, such as targeting specific organisms, or minimizing protein changes in the substance being treated. Thus, if it is desirable to pressure process a substance at low temperatures, the carrier may be insulated with a material having minimum adiabatic heating characteristics, thereby preventing the product from absorbing heat from the vessel walls. In some situations, for example if the substance being processed is at a lower temperature than the freezing point of the pressure media prior to pressurization, it may be desirable to separate the pressurizing media from the product. The insulated carrier may then be provided with a floating piston, diaphragm or a bladder to allow pressurization of the colder product by the pressure media while isolating the media from the product.

From the foregoing it will be appreciated that, although specific embodiments of the invention have been described herein for purposes of illustration, various modifications may be made without deviating from the spirit and scope of the invention. For example, it will be understood that the various components and steps of the systems described above may be used in various combinations with each other. Accordingly, the invention is not limited except as by the appended claims.

The invention claimed is:

1. A method for pressure processing a product comprising:
   loading the product into a product carrier insulated with a material having adiabatic heating properties by which the material exhibits a compression temperature change of 3-10° C. for a 100 MPa pressure change;
   inserting the product carrier and the product contained therein into an ultrahigh-pressure vessel;
   pressurizing the product carrier and its contents with a volume of pressure media for a selected period of time; and
   removing the product carrier from the ultrahigh-pressure vessel.

2. The method according to claim 1, further comprising:
   preheating the product in the product carrier to a selected temperature;
   preheating the ultrahigh-pressure vessel to the selected temperature; and
   preheating the pressure media to the selected temperature, prior to pressurizing the product carrier.

3. The method according to claim 2, further comprising: insulating an exterior surface of the product carrier as it is moved from a preheating apparatus to the ultrahigh-pressure vessel.

4. The method according to claim 1, further comprising: preheating the ultrahigh-pressure vessel to a first temperature that is higher than an initial temperature of the product prior to pressurizing the product carrier.

5. The method according to claim 4 wherein the first temperature is equal to the expected temperature of the product when pressurized.

6. The method according to claim 1, further comprising:
   adding a quantity of pressure media into the product carrier with the product prior to inserting the product carrier into the ultrahigh-pressure vessel.

7. A method for pressure processing a product comprising:
   loading the product into a product carrier that is insulated with a material and substantially fluidically closed, the material having adiabatic heating properties by which the material exhibits a compression temperature change of 3-10° C. for a 100 MPa pressure change;
   preheating an ultrahigh-pressure vessel to a selected temperature that is higher than an initial temperature of the product prior to pressurizing the product carrier;
   inserting the product carrier into the ultrahigh-pressure vessel;
   allowing pressure media to flow into the product carrier through selected pressure media entry ports;
   pressurizing the product carrier with the pressure media for a selected period of time; and
   removing the product carrier from the ultrahigh-pressure vessel.

8. The method according to claim 7, further comprising: insulating an exterior surface of the product carrier as the product carrier is moved from a preheating apparatus to the ultrahigh-pressure vessel.

9. The method according to claim 7, wherein the selected temperature is equal to the expected temperature of the product when pressurized.

10. A method for pressure processing a product comprising:
    loading the product into a product carrier that is insulated with a material having adiabatic heating properties by which the material exhibits a compression temperature change of 3-10° C. for a 100 MPa pressure change;
    closing the product carrier to substantially prevent the flow of pressure media into and out of the product carrier except through selected pressure media entry ports;
    inserting the product carrier into an ultrahigh-pressure vessel;
    preheating the ultrahigh-pressure vessel to a first temperature that is higher than an initial temperature of the product prior to pressurizing the product carrier;
    pressurizing the product carrier for a selected period of time; and
    removing the product carrier from the ultrahigh-pressure vessel.

11. The method according to claim 10, further comprising:
    inserting the product carrier into the ultrahigh-pressure vessel and substantially simultaneously allowing a volume of pressure media to enter the pressure vessel.

12. The method according to claim 11, further comprising:
    adding a quantity of pressure media in the product carrier prior to inserting the product carrier into the ultrahigh-pressure vessel.

13. The method according to claim 10, further comprising:
    adding a quantity of pressure media in the pressure carrier prior to inserting the product carrier into the ultrahigh-pressure vessel.

14. A method for pressure processing of product comprising:
    loading the product into a product carrier that is insulated with a material having adiabatic heating properties by which the material exhibits a compression temperature change of 3-10° C. for a 100 MPa pressure change;
    closing the product carrier to substantially prevent the flow of pressure media into and out of the product carrier except through one or more selected pressure media entry ports;
    preheating the product, an ultrahigh-pressure vessel and a volume of pressure media to a selected temperature;
    inserting the product carrier into the ultrahigh-pressure vessel;
    pressurizing the product with the pressure media for a selected period of time;
    removing the product carrier from the ultrahigh-pressure vessel;
    evacuating the pressure media from the ultrahigh-pressure vessel to a reservoir;
    reheating the pressure media in the reservoir to a selected temperature; and
    allowing the pressure media from the reservoir to flow into the pressure vessel for treatment of a second batch of product.

15. The method according to claim 14, further comprising:
    adding a quantity of pressure media into the product carrier prior to inserting the product carrier into the ultrahigh-pressure vessel.

* * * * *